United States Patent [19]

Chakrabarti

[11] 4,233,229

[45] Nov. 11, 1980

[54] PREPARATION OF SALT-FREE N-ACYL TAURINES

[75] Inventor: Paritosh M. Chakrabarti, Wayne, N.J.

[73] Assignee: GAF Corporation, New York, N.Y.

[21] Appl. No.: 866,284

[22] Filed: Jan. 3, 1978

[51] Int. Cl.$^2$ ............................................ C07C 143/90
[52] U.S. Cl. ................................ 260/401; 260/507 R; 260/513 N
[58] Field of Search ................ 260/401, 513 N, 507 R

[56] References Cited

U.S. PATENT DOCUMENTS

| | | | |
|---|---|---|---|
| 2,844,611 | 7/1958 | Freudenberg | 260/404 |
| 2,987,526 | 6/1961 | Schenck | 260/401 |

Primary Examiner—John F. Niebling
Attorney, Agent, or Firm—Walter C. Kehm; James Magee; Sheldon Parker

[57] ABSTRACT

A process for preparing a substantially salt free N-acyl taurine by reacting 1 mole of a higher molecular weight carboxylic acid chloride with 1 mole of a taurine salt containing at least 1 N-bonded H atom in a lower alkanol initially containing no more than about 15% by weight of water and about 1 mole of an alkali metal hydroxide at elevated temperatures, preferably at reflux, separating the insoluble precipitated alkali metal chloride from the alkanolic reaction medium at a temperature high enough to solubilize the N-acyl taurine reaction product, and cooling the reaction medium low enough to precipitate the desired N-acyl taurine.

11 Claims, No Drawings

PREPARATION OF SALT-FREE N-ACYL TAURINES

This invention relates to an improved method for making N-acylated taurines and more particularly to such a method productive of N-acylated taurines substantially free of salt.

The Schotten-Baumann reaction is a well known and highly useful means for acylating taurine compounds by reaction therewith of a carboxylic acid chloride in the presence of alkali. This reaction may be illustrated by the following equation:

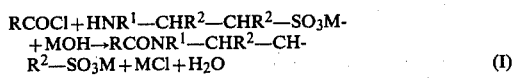

wherein
R is a $C_{5-19}$ hydrocarbon radical,
$R^1$ is H or a $C_{1-6}$ hydrocarbon radical,
$R^2$ is independently H, methyl or ethyl, and
M is alkali metal, e.g. Li, K, or preferably Na.

It is apparent that in the above reaction for the production of Igepon T type (GAF Corporation) anionic surfactants, a considerable quantity of salt is produced as a by-product. The presence of common salt as a contaminant in anionic surface active agents of the "Igepon" type has been recognized not only by the patentees of U.S. Pat. No. 1,932,180, particularly Example 37 and the description thereafter, but also by the teachings of German Pat. No. 664,309, in which an attempt was made to prepare an anionic surface active agent free from salt by reacting the fatty acid amide with a chloroethane sulfonic acid salt in an inert medium capable of dissolving the desired "Igepon," filtering the "Igepon" free from salt and recovering the salt-free "Igepon" by evaporation of the filtrate. Inasmuch as contamination by inorganic salts in commercial "Igepons" is of ever increasing importance due to their corrosive effect in the packaging of heavy duty liquid detergents, adverse hygroscopic and/or taste effect in synthetic soap bars, toothpastes and mold lubricants, and undesirability in certain emulsion polymerization reactions, renewed activity and efforts have been made to devise processes which would yield salt-free products.

In PB Report No. 70,344 T H K Scientific Exchange, Hoechst No. 154 and Register No. Ho 43/4, by Dr. Frank, there is described the preparation of "Igepons" by dehydrating a mixture of fatty acid and the sodium salt of methyl taurine at temperatures exceeding 200° C. producing a salt-free product. Dr. Frank states in the report that it seems of importance to prepare "Igepon" derivatives of the taurine series free from sodium chloride, since the salt content of technical "Igepon T" powder products is the main cause of their great hygroscopicity, and a new procedure for their preparation without this contaminant would therefore represent an important progress. In conclusion, Dr. Frank states that procedures described in PB No. 70,344 were unsatisfactory from another viewpoint. A separation of methylamine or ammonia was unavoidable during the thermal dehydration procedure, being detrimental to both yield and quality of the product. Furthermore, an additional step is required to recover reaction components lost by the inherent distillation of the fatty acid at the high temperatures necessary to promote the reaction.

As outlined by Dr. Frank, a careful selection of fatty acids is required to prevent undesirable discoloration of the fat moiety at elevated temperatures, as well as highly specialized equipment requirements. A study of the prior art relating to salt-free "Igepons" invariably shows either the taurine or fatty acid must be used in a large molar excess to promote the reaction to upwards of 90% completion.

A more startling revelation of salt content in common commercial "Igepons" derived from fatty acids and methyl taurine is taught by Kastens et al., Ind. and Eng. Chem., vol. 42; September-December 1950; pp. 1628-1638. As noted in Kastens et al., p. 1630, column 2, a mole of salt (sodium chloride) is formed for every mole of "Igepon." By weight ratio, this corresponds to 56 lbs. of salt for each 425 lbs. of their "IgeponT."

In addition to the by-product salt (MCl) produced in the above reaction I, other possible impurities include soaps (RCOOM), free fatty acids (RCOOH), unreacted starting materials and the like, and in the instant process, fatty acid esters of the alkanol employed as the reaction medium.

In U.S. Pat. No. 2,987,526 directed to a process for preparing salt-free N-acyl taurines, the reaction is carried out in acetone, dioxane or methylethyl ketone containing up to 15% water at reflux, cooled to about 20° C., diluted with water to dissolve NaCl and other water soluble impurities, and the precipitated Igepon T product filtered off and washed with water. This process involves relatively expensive solvents and other disadvantages, procedural and otherwise.

U.S. Pat. No. 2,844,611 is directed to improving the product yield and reducing the amount of soap impurities by carrying out the acylation reaction in an essentially aqueous medium, to which a minor amount of lower alkanol is added, at below 50° C. This process does not purport to yield a salt free product, the reaction yielding a slurry of the N-acyl taurine in a presumably salt-containing medium.

In related U.S. Pat. No. 2,844,610 with a similar objective, the acylation reaction is carried out in an aqueous medium at below 50° C. whereafter a lower alkanol is added to precipitate the impurities which are filtered off.

It is an object of this invention to provide a process for producing N-acyl taurines which will not be subject to one or more of the disadvantages attributable to the above-discussed prior art.

Another object of the invention is the provision of such a process for producing N-acyl taurines relatively and/or substantially free of salt.

Still another object of the invention is the provision of such a process which is more economical and/or more readily controlled and/or more independent of impurities in the starting materials and the like.

Other objects and advantages will appear as the description proceeds.

The above and other objects are made attainable by this invention which includes a process for preparing an N-acyl taurine substantially free of alkali metal chloride comprising reacting, in a $C_{1-4}$ alkanol medium initially containing no more than about 15% by weight of water, at temperatures ranging from about 30° C. up to reflux, 1 mole of a $C_{6-22}$ carboxylic acid chloride with 1 mole of a taurine salt of the formula

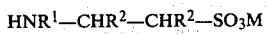 (II)

wherein
R¹ is H or a $C_{1-6}$ hydrocarbon radical,
R² is independently H, methyl or ethyl, and
M is alkali metal,
in the presence of about 1 mole of alkali metal hydroxide, separating the precipitated alkali metal chloride from the alkanolic reaction medium while maintaining the temperature thereof high enough to solubilize the N-acyl taurine reaction product, and then cooling the reaction medium low enough to precipitate the desired N-acyl taurine.

Any $C_{6-22}$ carboxylic acid chloride (RCOCl) may be employed in the process of this invention. Thus, the acid chloride may be derived from a saturated or unsaturated aliphatic, alicyclic or aliphatic aromatic acid. Acids of this type include caproic acid, isocaproic acid, enanthic acid, δ-methylhexylic acid, caprylic acid, ε-methylheptylic acid, dipropylacetic acid, pelargonic acid, δ-methyloctylic acid, capric acid, η-methylnonylic acid, isoamylisopropylacetic acid, undecylic acid, β-methyldecylic acid, di-tert.-butylmethylacetic acid, lauric acid, diisoamylacetic acid, tridecylic acid, myristic acid, pentadecylic acid, palmitic acid, di-n-heptylacetic acid, margaric acid, stearic acid, di-n-octylacetic acid, nondecylic acid, arachidic acid, behenic acid, γ-hexenoic acid, β-hexenoic acid, pyroterebic acid (4-methyl-β-pentenoic acid), α-ethylcrotonic acid, teracrylic acid, d-citronellic acid, θ-undecylenic acid, oleic acid, elaidic acid, erucic acid, brassidic acid, sorbic acid, stearolic acid, linolic acid, behenolic acid, ricinoleic acid and the like.

In addition to these acids, acids obtained from tall oil, hydrogenated tall oil, hydrogenated tallow, naphthenic, abietic and the like may be employed in the form of their acid chlorides. Alkyl benzoic acids, such as dodecyl benzoic acid, nonyl benzoic acid, alkyl naphthoic acids such as nonyl naphthoic acids and the like may be used in the form of their acid chlorides. Acid mixtures from various natural plant and animal oils, such as olive, tallow, castor, peanut, coconut, soybean, cottonseed, linseed, palm, corn, and the like may also be employed in the form of their acid chlorides.

Coco fatty acid chlorides are preferred, the coconut fatty acids being well known to comprise a mixture in which the $C_{12}$ acids are in highest proportion, lower proportions of $C_{14}$ acids, and decreasing proportions of acids of lower and higher carbon content, mostly saturated.

In the taurine salt reactant, R¹ may be H, cyclohexyl, normal or isomeric hexyl, amyl, butyl or propyl, ethyl, or preferably methyl. Examples of suitable taurines include:

| | |
|---|---|
| Taurine | N-butyl taurine |
| Ditaurine | N-isobutyl taurine |
| N-methyl taurine | N-tert.-butyl taurine |
| N-methyl ditaurine | N-amyl taurine |
| N-ethyl taurine | N-isoamyl taurine |
| N-propyl taurine | N-isopropyl taurine |

The salts of the foregoing taurines or 2-aminoalkane sulfonic acids are readily prepared by neutralization thereof with an equivalent amount of potassium or preferably sodium hydroxide or carbonate. Such salts may be reacted in substantially 100% form or in the form of an aqueous slurry or paste, provided of course that the addition of too much water to the reaction medium be avoided because of resulting undue solubilization of the salt by-product and other problems tending to preventing the attainment of the desired results herein. For example, the taurine salt, such as the N-methyl taurine sodium salt is commercially produced as an approximately 65% aqueous paste which is difficult and or expensive to dehydrate and is hence preferably employed in the form of the paste, i.e. in the form of an approximately 60–70% aqueous solution (i.e. paste).

Similarly, the alkali metal hydroxide reactant MOH may be employed in 100% powder, flake or other dry form, or in the form of a methanolic or aqueous solution, care being again taken to avoid introduction of too much water into the reaction medium. A fairly concentrated aqueous solution, e.g. of about 40–60%, preferably about 50%, concentration is often preferred to expedite admixture and solubilization in the reaction medium.

The $C_{1-4}$ alkanol employed in the instant process may be normal or isomeric butanol or propanol, ethanol, or preferably methanol, or any mixture thereof. The reaction medium initially may consist entirely of $C_{1-4}$ alkanol, or of aqueous solutions thereof containing no more than about 15% by weight of water to avoid undue solubilization of the by-product salt and other water soluble impurities, and other detrimental effects. A sufficient amount of alkanolic medium should be employed to yield a readily stirrable reaction medium and to solubilize the N-acyl taurine product at the elevated temperatures (e.g. reflux) at which the precipitated salt is separated. This generally calls for a solids content of about 10–35%, preferably about 20–25%.

The reaction involved herein is broadly summarized in the above "Abstract of the Invention". A slight excess, e.g. up to about 5% molar excess, of the acid chloride, or more preferably the taurine salt, reactant may be employed to assure a more complete reaction. Any elevated temperature may be employed in carrying out the reaction, as for example from about 30° C. up to reflux, although temperatures of about 30° C. to about 45° C., preferably about 35° C. to about 40° C., are more desirable to avoid undue discoloration of the product and the like. The pH of the reaction medium should be maintained over about 9, preferably up to about 10.5.

The order of addition of the reactants to the reactor is not critical, but in general it is preferred to first dissolve the taurine salt reactant in the alkanolic reaction medium and then gradually add the acid chloride reactant while agitating and maintaining the pH and temperature of the reaction medium as described above. The alkali metal hydroxide may be all dissolved in the initial solution of the taurine salt in alkanolic medium, or only a portion thereof so dissolved with the remainder added to the reaction medium along with the acid chloride reactant, or more preferably all added gradually along with the acid chloride reactant.

After all the reactants and alkali metal hydroxide have been added to the reaction medium, it is stirred at the indicated reaction temperatures for an additional period, e.g. up to about 1 or 2 hours, to assure completion of the reaction, indicated for example by cessation of change in pH, whereafter the reaction medium is heated to a temperature high enough to solubilize the acylated taurine product while the precipitated salt by-product (LiCl, KCl, or preferably NaCl) remains insoluble, preferably to reflux, maintained at such temperature for a period sufficient to maximize such solubilization, e.g. up to about 1 to 2 hours, and the salt then separated from the reaction medium while at or close to such solubilizing temperature, i.e. without permitting the temperature to fall significantly and thereby pro tanto undesirably precipitating the desired acylated taurine product.

The separation of the salt from the reaction medium may be accomplished in any desired manner, for example by centrifugal forces or preferably by filtration, more preferably by pressure filtration through a filter cell bed or the like, if desired with the assistance of a filter aid. To increase product recovery, the salt filter cake may be washed with hot fresh methanol, the wash liquor further treated to recover acylated taurine product therein, and the salt filter cake discarded.

The hot salt free reaction medium is then cooled without agitation to below about 5° C., preferably to about 3° C. or below, e.g. to about 0° C. or lower, and allowed to stand at such temperatures, e.g. up to about 0.5-1 hour, to maximize crystallization and precipitation of the desired N-acyl taurine product in substantially pure form. It should here be noted that the present process apparently also tends to reduce the undesired production of carboxylic acid soaps (alkali metal salts). The precipitated product may then be separated from the reaction medium in any desired manner, as by centrifugal forces and/or filtration at such temperatures below about 5° C. The mother liquor from the latter separation may be distilled to recover methanol the fraction between 63° C. and 68° C., and possibly a small amount of residual N-acyl taurine product.

For increased recovery, the aforementioned precipitated and separated product may be suspended in the wash liquor from the salt separation step, the liquor heated with agitation at about 50° C. or more for up to about 0.5 hour or more and then again cooled without agitation to below about 5° C. to crystallize and precipitate the N-acyl taurine product. The latter product may then be separated from the mother liquor in known manner, and dried. The latter mother liquor may be distilled to recover the methanol fraction (63°-68° C.) and an additional small crop of residual N-acyl taurine product.

The following example is only illustrative of a preferred embodiment of this invention and is not to be regarded as limitative. All amounts and proportions referred to herein and in the appended claims are by weight unless otherwise indicated.

EXAMPLE 1

A. Into a reaction kettle is charged 1290 lbs. of a 65% aqueous paste of N-methyl taurine sodium salt (5.0 moles) and 5500 lbs. of methanol, and the contents agitated for about 15 minutes to solution (slightly cloudy). With the contents vigorously agitated and maintained at 30°-40° C., 1130 lbs. of coconut fatty acid chloride (Av. M.W. 226, 5.0 moles) are gradually added over a period of about 5-6 hours. About 1 hour after starting such addition, 400 lbs. of a 50% aqueous solution of NaOH (5.0 moles) are gradually added to the reaction medium with the acid chloride at a rate sufficient to maintain a pH of over 9, typically 9-10.5, in the reaction medium.

B. When the entire amount of acid chloride and NaOH solution has been added, the reaction medium is stirred at about 35°-40° C. for another hour, gradually heated to reflux (about 65° C.), refluxed with agitation for about 1 hour, and pressure filtered through a filter cell bed while keeping the temperature as close to the reflux temperature as possible (i.e. no more than about 5° C. lower).

C. The filtrate from B is cooled to 0°-3° C. without agitation, kept standing at that temperature for about 0.5 hour, and the precipitated crystalline N-coconut fatty acyl-N-methyl taurine, sodium salt reaction product separated from the reaction medium by filtering or centrifuging through filter paper or fine mesh filter cloth at 0°-3° C. This product (filter cake) may be dried and used as such.

D. The salt filter cake from B is washed with about 1,000 lbs. of hot fresh methanol (50°-60° C.) and discarded. Into the resulting methanol wash liquor is mixed the filter cake product from C., and the mixture heated with agitation to about 50° C., cooled without agitation to about 0°-3° C., held at that temperature for about 0.5 hour, and the precipitated crystalline substantially pure product separated as by filtration and dried.

E. The mother liquors (filtrates) from C and D are separately or together distilled to recover the methanol fraction collected at 63°-68° C. and additional crops of the desired N-acyl taurine product in the residue.

The desired reaction product of the above procedure is substantially salt-free, i.e. contains a maximum of about 1.5% sodium chloride.

With suitable adjustments of reaction and reflux temperatures, the procedure of Example 1 is repeated, with similar results, using equivalent amounts and proportions of other $C_{6-22}$ carboxylic acid chlorides, taurine salts, alkali metal hydroxides, and/or $C_{1-4}$ alkanols.

This invention has been disclosed with respect to preferred embodiments, and it will be understood that various modifications and variations thereof obvious to those skilled in this art are to be included within the spirit and purview of this application and the scope of the appended claims.

What is claimed is:

1. A process for preparing an N-acyl taurine substantially free of alkali metal chloride comprising reacting, in a $C_{1-4}$ alkanol medium initially containing no more than about 15% by weight of water, at temperatures ranging from about 30° C. up to reflux, 1 mole of a $C_{6-22}$ carboxylic acid chloride with 1 mole of a taurine salt of the formula $$HNR^1-CHR^2-CHR^2-SO_3M$$

wherein
$R^1$ is H or a $C_{1-6}$ hydrocarbon radical,
$R^2$ is independently H, methyl or ethyl, and
M is alkali metal,
in the presence of about 1 mole of alkali metal hydroxide, separating the precipitated alkali metal chloride from the alkanolic reaction mixture while maintaining the temperature thereof high enough to solubilize the N-acyl taurine reaction product, and then cooling the reaction medium low enough to precipitate the desired N-acyl taurine.

2. A process as defined in claim 1 wherein said carboxylic acid chloride is derived from coconut fatty acids.

3. A process as defined in claim 1 wherein said taurine salt is the sodium salt of N-methyl taurine.

4. A process as defined in claim 1 wherein said alkali metal hydroxide is sodium hydroxide.

5. A process as defined in claim 1 wherein said alkanol is methanol.

6. A process as defined in claim 1 wherein the reaction is first carried out at about 30° to 45° C. and then at reflux until initiation of said separation step.

7. A process as defined in claim 6 wherein said carboxylic acid chloride is derived from coconut fatty acids.

8. A process as defined in claim 7 wherein said taurine salt is the sodium salt of N-methyl taurine.

9. A process as defined in claim 8 wherein said alkali metal hydroxide is sodium hydroxide.

10. A process as defined in claim 9 wherein said alkanol is methanol.

11. A process as defined in claim 1 wherein the taurine salt, in the form of an approximately 60 to 70% aqueous solution, is dissolved in methanol, and gradual addition to the resulting methanolic solution of the acid chloride is initiated whereafter the alkali metal hydroxide, in the form of an approximately 50% aqueous solution, is also gradually added to said methanolic solution, together with the remaining acid chloride, at a rate sufficient to maintain the pH of the reaction medium above 9.

* * * * *